United States Patent
Mu et al.

(10) Patent No.: US 12,049,655 B2
(45) Date of Patent: Jul. 30, 2024

(54) CONSTRUCTION METHOD AND APPLICATION OF MICROORGANISM CAPABLE OF REALIZING HIGH PRODUCTION OF LACTO-N-TETROSE

(71) Applicant: Jiangnan University, Wuxi (CN)

(72) Inventors: Wanmeng Mu, Wuxi (CN); Yingying Zhu, Wuxi (CN); Zeyu Li, Wuxi (CN); Wenli Zhang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/485,501

(22) Filed: Oct. 12, 2023

(65) Prior Publication Data

US 2024/0035057 A1 Feb. 1, 2024

Related U.S. Application Data

(63) Continuation of application No. PCT/CN2022/110181, filed on Aug. 4, 2022.

(30) Foreign Application Priority Data

Aug. 6, 2021 (CN) .......................... 202110900124.5

(51) Int. Cl.
C12P 19/04 (2006.01)
C12N 9/10 (2006.01)
C12N 15/70 (2006.01)

(52) U.S. Cl.
CPC ............ *C12P 19/04* (2013.01); *C12N 9/1051* (2013.01); *C12N 15/70* (2013.01); *C12Y 204/01102* (2013.01); *C12N 2800/101* (2013.01)

(58) Field of Classification Search
CPC ....... C12P 19/04; C12N 9/1051; C12N 15/70; C12N 2800/101; C12Y 204/01102
See application file for complete search history.

(56) References Cited

U.S. PATENT DOCUMENTS

2023/0313253 A1* 10/2023 Aesaert .................. C12P 19/12 435/97

FOREIGN PATENT DOCUMENTS

| CN | 111548979 A | 8/2020 | |
|---|---|---|---|
| CN | 111979168 A | * 11/2020 | ............... C12N 1/21 |
| CN | 111979168 A | 11/2020 | |
| CN | 113652385 A | 11/2021 | |
| CN | 113684164 A | 11/2021 | |
| WO | 2020058493 A1 | 3/2020 | |
| WO | 2022034075 A1 | 2/2022 | |
| WO | 2022034081 A1 | 2/2022 | |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Zhu et al., Physiological effects, biosynthesis, and derivatization of key human milk tetrasaccharides, lacto-N-tetraose, and lacto-N-neotetraose. Critical Rev. Biotechnol., 2022, vol. 42(4): 578-596; published online Aug. 4, 2021. (Year: 2022).*
Zhu et al., Metabolic Engineering of Escherichia coli for Lacto-N-triose II Production with High Productivity. J. Agric. Food Chem., 2021, vol. 69: 3702-3711. (Year: 2021).*
Zhu Y.Y. et.al. "Metabolic Engineering of Escherichia coli for Efficient Biosynthesis of Lacto N tetraose Using a Novel 1 3-Galactosyltransferase from Pseudogulbenkiania ferrooxidans.", J.Agric.Food.Chem., vol. 16, Aug. 26, 2021. p. 11342-11349.
Chen, Jian et al. "Advances in Biosynthesis of Breast Milk Oligosaccharides" J. Chinese Institute of Food Science and Technology. vol. 16 No. 11. Nov. 30, 2016.
"Genbank:Yingying Zhu glycosyltransferase [Pseudogulbenkiania ferrooxidans].", NCBI Genbank, (Aug. 3, 2021).

* cited by examiner

*Primary Examiner* — Ganapathirama Raghu
(74) *Attorney, Agent, or Firm* — IPRO, PLLC

(57) ABSTRACT

Disclosed are a construction method and application of a microorganism capable of realizing high production of lacto-N-tetrose, belonging to the field of microbial genetic engineering. The present disclosure employs a strain which has been constructed in the early stage for efficiently producing a precursor lacto-N-triose II as an original strain to synthesize a key gene of the lacto-N-tetrose via overexpression, thus enabling the strain to have a synthesis capability of producing the lacto-N-tetrose. The present disclosure improves the synthesis of the lacto-N-tetrose by screening a high-efficiency β-1,3-galactosyl transferase gene, and reasonably designing the co-expression of the β-1,3-galactosyl transferase gene and a key UDP-glucose 4 epimerase gene (galE) for strengthening a UDP-galactose pathway on a vector pCDFDuet-1. In a shake flask experiment, the lacto-N-tetrose production capacity of *Escherichia coli* is 3.04 g/L. The lacto-N-tetrose yield in a 3 L fermentation tank reaches 25.49 g/L. Therefore, the microorganism has an industrial application prospect.

12 Claims, 4 Drawing Sheets

Specification includes a Sequence Listing.

SEQUENCE LISTING

```
Sequence total quantity: 38
SEQ ID NO: 1           moltype = DNA   length = 1338
FEATURE                Location/Qualifiers
source                 1..1338
                       mol_type = other DNA
                       organism = synthetic construct
SEQUENCE: 1
atgagtaatc gtaaatattt cggtaccgat gggattcgtg gtcgtgtagg ggatgcgccg   60
atcacacctg attttgtgct taagctgggt tgggccgcgg gtaaagtgct ggcgcgccac  120
ggctcccgta agattattat tggtaaagac acgcgtattt ctggctatat gctggagtca  180
gcactggaag cgggtctggc ggcagcgggc cttccgcac tcttcactgg cccgatgcca   240
acaccggccg tggcttatct gacgcgtacc ttccgcgcag aggccggaat tgtgatatct  300
gcatcgcata cccgttctta cgataatggc attaaattct tctctatcga cggcaccaaa  360
ctgccggatg cggtagaaga ggccatcgaa gcggaaatgg aaaaggagat cagctgcgtt  420
gattcggcag aactgggtaa agccagccgt atcgttgatc ccgcgggtcg ctatatcgag  480
ttttgcaaag ccacgttccc gaacgaactt agcctcagtg aactgaagat tgtggtggat  540
tgtgcaaacg gtgcgactta tcacatcgcg ccgaacgtgc tgcgcgaact gggggcgaac  600
gttatcgcta tcgttgtga ccaaacggt gtaaacatca atgccgaagt gggggctacc   660
gacgttcgcg cgctccaggc tcgtgtgctg gctgaaaaag cggatctcgg tattgccttc  720
gacggcgatg gcgatcgcgt gattatggtt gaccatgaag gcaataaagt cgatggcgat  780
cagatcatgt atatcatcgc gcgtgaaggt cttcgtcagg gccagctgcg tggtggcgct  840
gtgggtacat tgatgagcaa catggggctt gaactggcgc tgaaacagtt aggaattcca  900
tttgcgccg cgaaagtggg tgaccgctac gtactggaaa aatgcagga gaaaggctgg   960
cgtatcggtg cagagaattc cggtcatgtg atcctgctgg ataaaactac taccggtgac 1020
ggcatcgttg ctggcttgca ggtgctggcg gcgatggcac gtaaccatat gagcctgcac 1080
gacctttgca gcggcatgaa aatgttcccg cagattctgg ttaacgtacg ttacaccgca 1140
ggtagcggcg atccacttga gcatgagtca gttaaagccg tgaccgcaga ggttgaagct 1200
gcgctgggca accgtggacg cgtgttgctg cgtaaatccg gcaccgaacc gttaattcgc 1260
gtgatggtgg aaggcgaaga cgaagcgcag gtgactgaat ttgcacaccg catcgccgat 1320
gcagtaaaag ccgttttaa                                              1338

SEQ ID NO: 2           moltype = DNA   length = 1371
FEATURE                Location/Qualifiers
source                 1..1371
                       mol_type = other DNA
                       organism = synthetic construct
SEQUENCE: 2
atgttgaata atgctatgag cgtagtgatc cttgccgcag gcaaaggcac gcgcatgtat   60
tccgatcttc cgaaagtgct gcataccctt gccgggaaag cgatggttca gcatgtcatt  120
gatgctgcga atgaattagg cgcagcgcac gttcacctgg tgtacggtca cggcggcgat  180
ctgctaaaac aggcgctgaa agacgacaac cttaactggg tgcttcaggc agagcagctg  240
ggtacgggtc atgcaatgca gcaggccgca cctttctttg ccgatgatga agacatttta  300
atgctctacg cgacgtgcc gctgatctct gtcgaaacac tccagcgtct gcgtgatgct  360
aaaccgcagg gtggcattgg tctgctgacg gtgaaactgg atgatccgac ggttatggaa  420
cgtatcaccc gtgaaaacgg caaagttacc ggcattgttg agcacaaaga tgccaccgac  480
gagcagcgtc agattcagga gatcaacacc ggcattctga ttgccaacgg cgcagatatg  540
aaacgctggc tggcgaagct gaccaacaat aatgctcagg gcgaatacta catcaccgac  600
attattgcgc tggcgtatca ggaagggcgt gaaatcgtcc ccgttcatcc gcaacgttta  660
agcgaagtag aaggcgtgaa taaccgcctg caactctccc gtctggagcg tgtttatcag  720
tccgaacagg ctgaaaaact gctgttagca ggcgttatgc tgcgcgatcc agcgcgtttt  780
gatctgcgtg gtacgctaac tcacgggcgc gatgttgaaa ttgatactaa cgttatcatc  840
gagggcaacg tgactctcgg tcatcgcgtg aaaattggca ccggttgcgt gattaaaaac  900
agcgtgattg gcgatgattg cgaaatcagt cctgataccg ttgtggaaga tgcgaatctg  960
gcagcggcct gtaccattgg cccgtttgcc cgtttgcgtc tggtgctga gttgctggaa  1020
ggtgctcacg tcggtaactt cgttgagatg aaaaagcgc gtctgggtaa aggctcgaaa  1080
gctggtcatc tgacttacct gggcgatgcg gaaattggcg ataacgttaa catcggcgcg 1140
ggaaccatta cctgcaacta cgatgtgcg aataaattta agaccattat cggcgacgat 1200
gtgtttgttg gttccgacac tcagctggtg gccccggtaa cagtaggcaa aggcgcgacc 1260
attgctgcgg gtacaactgt gacgcgtaat gtcggcgaaa atgcattagc tatcagccgt 1320
gtgccgcaga ctcagaaaga aggctggcgt cgtccggtaa agaaaaagtg a           1371

SEQ ID NO: 3           moltype = DNA   length = 1830
FEATURE                Location/Qualifiers
source                 1..1830
                       mol_type = other DNA
                       organism = synthetic construct
SEQUENCE: 3
atgtgtggaa ttgttggcgc gatcgcgcaa cgtgatgtag cagaaatcct tcttgaaggt   60
ttacgtcgtc tggaataccg cggatatgac tctgccggtc tggccgttgt tgatgcagaa  120
ggtcatatga cccgcctgcg tcgcctcggt aaagtccaga tgctggcaca ggcagcggaa  180
gaacatcctc tgcatggcgg cactggtatt gctcacactc gctgggcgac ccacggtgaa  240
ccttcagaag tgaatgcgca tccgcatgtt ctgaacaca ttgtggtggt gcataacggc   300
atcatcgaaa accatgaacc gctgcgtgaa gagctaaaag cggtgggcta taccttcgtt  360
tctgaaaccg acaccgaagt gattgccat ctggtgaact gggagcgtgaa acaaggcggg  420
actctgcgtg aggccgttct gcgtgctatc cgcagctgc gtggtgcgta cggtacagtg  480
atcatggact cccgtcaccc ggataccctg ctggcggcac gttctggtag tccgctggtg  540
attggcctgg gatgggcga aaacttatc gcttctgacc agctggcgct gttgccggtg   600
acccgtcgct tatcttcct tgaagagggc gatattgcgg aaatcactcg ccgttcggta  660
```

```
aacatcttcg ataaaactgg cgcggaagta aaacgtcagg atatcgaatc caatctgcaa   720
tatgacgcgg gcgataaagg catttaccgt cactacatgc agaaagagat ctacgaacag   780
ccgaacgcga tcaaaaacac ccttaccgga cgcatcagcc acggtcaggt tgatttaagc   840
gagctgggac cgaacgccga cgaactgctg tcgaaggttg agcatattca gatcctcgcc   900
tgtgtgactt cttataactc cggtatggtt tcccgctact ggtttgaatc gctagcaggt   960
attccgtgcg acgtcgaaat cgcctctgaa ttccgctatc gcaaatctgc cgtgcgtcgt  1020
aacagcctga tgatcacctt gtcacagtct ggcgaaaccg cggataccct ggctggcctg  1080
cgtcgtcga aagagctggg ttaccttggt tcactggcaa tctgtaacgt tccgggttct  1140
tctctggtgc gcgaatccga tctggcgcta atgaccaacg cgggtacgaa aatcggcgtg  1200
gcatccacta aagcattcac cactcagtta actgtgctgt tgatgctggt ggcgaagctg  1260
tctcgcctga aaggtctgga tgcctccatt gaacatgaca tcgtgcatgg tctgcaggcg  1320
ctgccgagcc gtattgagca gatgctgtct caggacaaac gcattgaagc gctggcagaa  1380
gatttctctg acaaacatca cgcgctgttc ctgggccgtg gcgatcagta cccaatcgcg  1440
ctggaaggcg cattgaagtt gaaagagatc tcttacattc acgctgaagc ctacgctgct  1500
ggcgaactga aacacggtcc gctggcgcta attgatgccg atatgccggt tattgttgtt  1560
gcaccgaaca acgaattgct ggaaaaactg aaatccaaca ttgaagaagt tcgcgcgcgt  1620
ggcggtcagt tgtatgtctt cgccgatcag gatgcgggtt ttgtaagtag cgataacatg  1680
cacatcatcg agatgccgca tgtggaagag gtgattgcac cgatcttcta caccgttccg  1740
ctgcagctgc tggcttacca tgtcgcgctg atcaaaggca ccgacgttga ccagccgcgt  1800
aacctggcaa aatcggttac ggttgagtaa                                   1830

SEQ ID NO: 4           moltype = DNA  length = 1005
FEATURE                Location/Qualifiers
source                 1..1005
                       mol_type = other DNA
                       organism = synthetic construct
SEQUENCE: 4
atgggccagc cgctggttag cgttctgatc tgcgcgtaca acgttgaaaa atatttcgcg    60
cagagcctgg cagctgttgt taaccagacc tggcgtaacc tggacattct gatcgttgat   120
gatgcctcta ccgatggcac cctggcgatc cgcgcagcgt tccaggaaca ggacggtcgg   180
atccgtattc tggcgcagcc gcgtaactct ggtctgattc caagcctgaa catcggcctg   240
gatgaactgg cgaaaagcgg cggtggtggt gaatacatcg cgcgtaccga tgcggatgat   300
atcgcagctc cggattggat tgaaaaaatc gttggtgaaa tggaaaaaga tcgtagcatc   360
atcgcaatgg gcgcttggct ggaagtgctg tcccgaagaaa aagatggcaa ccgtgcggca   420
cgtcaccacg aacacggtaa aatctggaaa aaaccgaccc gtacgcaaga catcgcggat   480
ttcttcccat tcggcaaccc gattcacaac aacaccatga tcatgcgtcg ttccgtgatc   540
gatgcgggcc tgcgttacaa caccgaacgt gattgggcag aagactatca gttctggtat   600
gatgtttcta aactgggtcg tctggcgtac tacccggaag cgctggttaa ataccgtctg   660
cacgctaacc aggttagctc caaatatagc atccgcacgg acgaaatcgc tcagggtatc   720
cagaaaaccg cacgtaacga tttcctgcag tctatgggtt tcaaaacccg tttcgatagc   780
ctggaatacc gtcagattaa agcggttgcg tatgaactgc tggaaaaaca cctgccggaa   840
gaagattttg aactggcgcg tcgtttcctg taccagtgct tcaaacgtac cgataccctg   900
ccggcgggcg cttggctgga tttcgcggcg gatggccgta tgcgtcgtct gttcaccctg   960
cgtcagtact tcggtatcct gcaccgtctg ctgaaaaacc gttaa                  1005

SEQ ID NO: 5           moltype = DNA  length = 828
FEATURE                Location/Qualifiers
source                 1..828
                       mol_type = other DNA
                       organism = synthetic construct
SEQUENCE: 5
atggataaaa tcaaacaggg tagcgctagc ctggttgttg gtgatcagca ggaaaaacac    60
ccggttgtta gcgttctgct gccggttaac cgtgttgatc gtttcttcat cccggcggtt   120
gaatctatcc tgacccagac cctgcaggat ttcgaactga tcattatcgc taacggttgc   180
agcaccgaac acctgaacaa aatccgtctg acctacggtg atcacaaccg cgttcgtatc   240
ctgaacaccg aaatcaaagg cctgccgttc gcgctgaacc tgggtgttca caacgcgcgt   300
ggcctgtaca tcgcgcgtat ggatgcggat gatatctcta tcccggaacg tctgaaaaaa   360
cagctgaaca ccctggaaca gaacaagaaa tcggcgtttt ttctagcgg tgttgatttc   420
atcgatgaaa acgatcaggc gatccgtgaa ggcaaattcc cggaactgac cgataaagat   480
caccgtcgtc tgctgccgct gatctgctgc atcgcgcacc gaccgttat ggttcgtaaa   540
gaaatcatca acaaactggg tggttacagc ttcggcagct tcagcgaaga ttacgatctg   600
tggctgcgta tcatgcgtga actgccgaaa gttgaattct accgtatccc ggaatccctg   660
ctgaaatacc gtcgtcacgg taaccaggct accagcagca aaaacatcaa aaagatccgt   720
gcgtacaact ctgcgctgaa aatctgtgaa ctgttcctga gccgtaaact gaaattcatc   780
atcggtatca tcctgccggc gcgtatggtg accctggcc gtaaataa                828

SEQ ID NO: 6           moltype = DNA  length = 1017
FEATURE                Location/Qualifiers
source                 1..1017
                       mol_type = other DNA
                       organism = synthetic construct
SEQUENCE: 6
atgagagttc tggttaccgg tggtagcggt tacattggaa gtcatacctg tgtgcaatta    60
ctgcaaaacg gtcatgatgt catcattctt gataacctct gtaacagtaa gcgcagcgta   120
ctgcctgtta tcgagcgttt aggcggcaaa catccaacgt ttgttgaagg cgatattcgt   180
aacgaagcgt tgatgaccga gatcctgcac gatcacgcta tcgacaccgt gatccacttc   240
gccgggctga aagccgtggg cgaatcggta caaaaaccgc tggaatatta cgacaacaat   300
gtcaacggca ctctgcgcct gattagcgcc atgcgcgccg ctaacgtcaa aaacttttat   360
tttagctcct ccgccaccgt ttatggcgat cagcccaaaa ttccatacgt tgaaagcttc   420
```

```
ccgaccggca caccgcaaag cccttacggc aaaagcaagc tgatggtgga acagatcctc    480
accgatctgc aaaagcccca gccgactgga agcattgccc tgctgcgcta cttcaacccg    540
gttggcgcgc atccgtcggg cgatatgggc gaagatccgc aaggcattcc gaataacctg    600
atgccataca tcgcccaggt tgctgtaggc cgtcgcgact cgctggcgat ttttggtaac    660
gattatccga ccgaagatgg tactggcgta cgcgattaca tccacgtaat ggatctggcg    720
gacggtcacg tcgtggcgat ggaaaaactg gcgaacaagc caggcgtaca catctacaac    780
ctcggcgctg gcgtaggcaa cagcgtgctg gacgtggtta atgccttcag caaagcctgc    840
ggcaaaccgg ttaattatca ttttgcaccg cgtcgcgagg cgaccttcc ggcctactgg     900
gcggacgcca gcaaagccga ccgtgaactg aactggcgcg taacgcgcac actcgatgaa    960
atggcgcagg cacctggca ctggcagtca cgccatccac agggatatcc cgattaa      1017
```

SEQ ID NO: 7          moltype = DNA  length = 798
FEATURE                Location/Qualifiers
source                 1..798
                         mol_type = other DNA
                         organism = synthetic construct
SEQUENCE: 7

```
atgatcatcg atgaagcgga aagcgcggaa agcaccccac cggtggttag cgtgatcctg    60
ccggtgaaca agaaaaaccc gttcctggat gaagcgatca acagcatcct gagccagacc    120
ttcagcagct tcgaaatcat catcgtggcg aactgctgca ccgacgactt ctacaacgaa    180
ctgaaacaca agtgaacga taaaatcaaa ctgatccgta ccaacatcgc gtacctgccg    240
tacagcctga acaaagcgat cgacctgagc aacggcaagt tcatcgcgcg tatggattcc    300
gacgatatca gccacccgga tcgcttcacc aaacaggttg acttcctgaa aaacaacccg    360
tacgttgacg tggttggcac caacgcgatc ttcatcgacg ataaaggccg tgaaatcaac    420
aaaaccaaac tgccggaaga aaacctggac atcgtgaaaa acctgccgta caatgctgc     480
atcgttcacc cgagcgttat gttccgtaaa aagttatcg acgcatcgg tggttacatg     540
ttcagcaact acagcgaaga ttacgaactg tggaaccgtc tgtctctggc gaaaatcaaa    600
ttccagaacc tgccggaata cctgttctac taccgtctgc acgaaggcca gagcaccgcg    660
aaaaagaacc tgtacatggt tatggttaac gatctggtta tcaaaatgaa atgcttcttc    720
ctgaccggca acatcaacta cctgttcggc ggcatccgta ccatcgcgag cttcatctac    780
tgcaaataca tcaaataa                                                 798
```

SEQ ID NO: 8          moltype = DNA  length = 789
FEATURE                Location/Qualifiers
source                 1..789
                         mol_type = other DNA
                         organism = synthetic construct
SEQUENCE: 8

```
atggatacca tcatgatcaa acgtccgctg gttagcgtta tcctgccggt taacaaaaac    60
aacccgcacc tggaagaagc gatccagagc atcaaaaacc agacctacaa agaactggaa    120
ctgatcatca tcgctaacaa ctgcgaagat aacttctaca gccgctgct gaaataccag     180
gatcagaaaa ccaaaatcat ccgtaccagc atcaaatacc tgccgttcag cctgaacctg    240
ggcgttcacc tgagccaggg cgaatacatc gcgcgtatgg attccgatga tatcagcgtt    300
ctggatcgta tcgaaaaaca ggttaaacgt ttcctgaaca cccggaact gtccatcctg      360
ggttctaacg tggaatacat caacgaagcg tccgaaagca tcggttacag caactaccgg    420
ctggatcact ctagcatcgt taactctttc cgttccgtt gcaacctggc gcacccgacc     480
atcatggtta aaaagaagt gatcaccacc ctgggcggct acatgtacgg tagcctgtcc     540
gaagattacg atctgtggat ccgcgcgtct cgccacgata acttcaaatt cagcaacatc    600
gatgaaccgc tgctgaaata ccgcatccac aaaggccagg cgaccaacaa atctaacgcg    660
tacaacatct tcgcgttcga tagctctctg aaaatccgtg aattcctgct gaacggtaac    720
gtgcagtacc tgctgggcgc ggcgcgtggc ttcttcgcgt tcctgtacgt tcgtttcatc    780
aaaaaataa                                                           789
```

SEQ ID NO: 9          moltype = AA  length = 275
FEATURE                Location/Qualifiers
source                 1..275
                         mol_type = protein
                         organism = Pseudogulbenkiania ferrooxidans
SEQUENCE: 9

```
MDKIQGSAS  LVVGDQQEKH  PVVSVLLPVN  RVDRFFIPAV  ESILTQTLQD  FELIIIANGC    60
STEHLNKIRL TYGDHNRVRI LNTEIKGLPF ALNLGVHNAR GLYIARMDAD DISIPERLEK    120
QLNTLEQNKK IGVVSSGVDF IDENDQAIRE GKFPELTDKD HRRLLPLICC IAHPTVMVRK    180
EIINKLGGYS FGSFSEDYDL WLRIMRELPE VEFYRIPESL LKYRRHGNQA TSSKNIKKIR    240
AYNSALKIRE LFLSRKLKFI IGIILPARMV TLWRK                              275
```

SEQ ID NO: 10         moltype = DNA  length = 31
FEATURE                Location/Qualifiers
source                 1..31
                         mol_type = other DNA
                         organism = synthetic construct
SEQUENCE: 10

```
cggaattcgt tcacacagga aacctataat g                                  31
```

SEQ ID NO: 11         moltype = DNA  length = 25
FEATURE                Location/Qualifiers
source                 1..25
                         mol_type = other DNA
                         organism = synthetic construct
SEQUENCE: 11

```
cggaattcaa gaaggagata taatg                                          25

SEQ ID NO: 12           moltype = AA  length = 376
FEATURE                 Location/Qualifiers
source                  1..376
                        mol_type = protein
                        organism = Escherichia coli
SEQUENCE: 12
MKVLTVFGTR PEAIKMAPLV HALAKDPFFE AKVCVTAQHR EMLDQVLKLF SIVPDYDLNI     60
MQPGQGLTEI TCRILEGLKP ILAEFKPDVV LVHGDTTTTL ATSLAAFYQR IPVGHVEAGL    120
RTGDLYSPWP EEANRTLTGH LAMYHFSPTE TSRQNLLREN VADSRIFITG NTVIDALLWV    180
RDQVMSSDKL RSELAANYPF IDPDKKMILV TGHRRESFGR GFEEICHALA DIATTHQDIQ    240
IVYPVHLNPN VREPVNRILG HVKNVILIDP QEYLPFVWLM NHAWLILTDS GGIQEEAPSL    300
GKPVLVMRDT TERPEAVTAG TVRLVGTDKQ RIVEEVTRLL KDENEYQAMS RAHNPYGDGQ    360
ACSRILEALK NNRISL                                                    376

SEQ ID NO: 13           moltype = AA  length = 266
FEATURE                 Location/Qualifiers
source                  1..266
                        mol_type = protein
                        organism = Escherichia coli
SEQUENCE: 13
MRLIPLTTAE QVGKWAARHI VNRINAFKPT ADRPFVLGLP TGGTPMTTYK ALVEMHKAGQ     60
VSFKHVVTFN MDEYVGLPKE HPESYYSFMH RNFFDHVDIP AENINLLNGN APDIDAECRQ    120
YEEKIRSYGK IHLFMGGVGN DGHIAFNEPA SSLASRTRIK TLTHDTRVAN SRFFDNDVNQ    180
VPKYALTVGV GTLLDAEEVM ILVLGSQKAL ALQAAVEGCV NHMWTISCLQ LHPKAIMVCD    240
EPSTMELKVK TLRYFNELEA ENIKGL                                         266

SEQ ID NO: 14           moltype = AA  length = 1024
FEATURE                 Location/Qualifiers
source                  1..1024
                        mol_type = protein
                        organism = Escherichia coli
SEQUENCE: 14
MTMITDSLAV VLQRRDWENP GVTQLNRLAA HPPFASWRNS EEARTDRPSQ QLRSLNGEWR     60
FAWFPAPEAV PESWLECDLP EADTVVVPSN WQMHGYDAPI YTNVTYPITV NPPFVPTENP    120
TGCYSLTFNV DESWLQEGQT RIIFDGVNSA FHLWCNGRWV GYGQDSRLPS EFDLSAFLRA    180
GENRLAVMVL RWSDGSYLED QDMWRMSGIF RDVSLLHKPT TQISDFHVAT RFNDDFSRAV    240
LEAEVQMCGE LRDYLRVTVS LWQGETQVAS GTAPFGGEII DERGGYADRV TLRLNVENPK    300
LWSAEIPNLY RAVVELHTAD GTLIEAEACD VGFREVRIEN GLLLLNGKPL LIRGVNRHEH    360
HPLHGQVMDE QTMVQDILLM KQNNFNAVRC SHYPNHPLWY TLCDRYGLYV VDEANIETHG    420
MVPMNRLTDD PRWLPAMSER VTRMVQRDRN HPSVIIWSLG NESGHGANHD ALYRWIKSVD    480
PSRPVQYEGG GADTTATDII CPMYARVDED QPFFAVPKWS IKKWLSLPGE TRPLILCEYA    540
HAMGNSLGGF AKYWQAFRQY PRLQGGFVWD WVDQSLIKYD ENGNPWSAYG GDFGDTPNDR    600
QFCMNGLVFA DRTPHPALTE AKHQQQFFQF RLSGQTIEVT SEYLFRHSDN ELLHWMVALD    660
GKPLASGEVP LDVAPQGKQL IELPELPQPE SAGQLWLTVR VVQPNATAWS EAGHISAWQQ    720
WRLAENLSVT LPAASHAIPH LTTSEMDFCI ELGNKRWQFN RQSGFLSQMW IGDKKQLLTP    780
LRDQFTRAPL DNDIGVSEAT RIDPNAWVER WKAAGHYQAE AALLQCTADT LADAVLITTA    840
HAWQHQGKTL FISRKTYRID GSGQMAITVD VEVASDTPHP ARIGLNCQLA QVAERVNWLG    900
LGPQENYPDR LTAACFDRWD LPLSDMYTPY VFPSENGLRC GTRELNYGPH QWRGDFQFNI    960
SRYSQQQLME TSHRHLLHAE EGTWLNIDGF HMGIGGDDSW SPSVSAEFQL SAGRYHYQLV   1020
WCQK                                                                1024

SEQ ID NO: 15           moltype = DNA  length = 33
FEATURE                 Location/Qualifiers
source                  1..33
                        mol_type = other DNA
                        organism = synthetic construct
SEQUENCE: 15
agcagccata tgatcatcga tgaagcggaa agc                                  33

SEQ ID NO: 16           moltype = DNA  length = 36
FEATURE                 Location/Qualifiers
source                  1..36
                        mol_type = other DNA
                        organism = synthetic construct
SEQUENCE: 16
gtgttatttg atgtatttgc agtagatgaa gctcgc                               36

SEQ ID NO: 17           moltype = DNA  length = 34
FEATURE                 Location/Qualifiers
source                  1..34
                        mol_type = other DNA
                        organism = synthetic construct
SEQUENCE: 17
tctcaattgg atgagagttc tggttaccgg tggt                                 34

SEQ ID NO: 18           moltype = DNA  length = 33
FEATURE                 Location/Qualifiers
```

-continued

```
source                     1..33
                           mol_type = other DNA
                           organism = synthetic construct
SEQUENCE: 18
gccgatattt aatcgggata tccctgtgga tgg                              33

SEQ ID NO: 19              moltype = DNA   length = 29
FEATURE                    Location/Qualifiers
source                     1..29
                           mol_type = other DNA
                           organism = synthetic construct
SEQUENCE: 19
tatcccgatt aaatatcggc cggccacgc                                   29

SEQ ID NO: 20              moltype = DNA   length = 31
FEATURE                    Location/Qualifiers
source                     1..31
                           mol_type = other DNA
                           organism = synthetic construct
SEQUENCE: 20
atgatcatat ggctgctgcc catggtatat c                                31

SEQ ID NO: 21              moltype = DNA   length = 37
FEATURE                    Location/Qualifiers
source                     1..37
                           mol_type = other DNA
                           organism = synthetic construct
SEQUENCE: 21
caaatacatc aaataacacc atcatcacca cagccag                          37

SEQ ID NO: 22              moltype = DNA   length = 40
FEATURE                    Location/Qualifiers
source                     1..40
                           mol_type = other DNA
                           organism = synthetic construct
SEQUENCE: 22
gaactctcat ccaattgaga tctgccatat gtatatctcc                       40

SEQ ID NO: 23              moltype = DNA   length = 36
FEATURE                    Location/Qualifiers
source                     1..36
                           mol_type = other DNA
                           organism = synthetic construct
SEQUENCE: 23
agcagccata tggataccat catgatcaaa cgtccg                           36

SEQ ID NO: 24              moltype = DNA   length = 38
FEATURE                    Location/Qualifiers
source                     1..38
                           mol_type = other DNA
                           organism = synthetic construct
SEQUENCE: 24
atggtgttat ttttgatga aacgaacgta caggaacg                          38

SEQ ID NO: 25              moltype = DNA   length = 34
FEATURE                    Location/Qualifiers
source                     1..34
                           mol_type = other DNA
                           organism = synthetic construct
SEQUENCE: 25
tctcaattgg atgagagttc tggttaccgg tggt                             34

SEQ ID NO: 26              moltype = DNA   length = 33
FEATURE                    Location/Qualifiers
source                     1..33
                           mol_type = other DNA
                           organism = synthetic construct
SEQUENCE: 26
gccgatattt aatcgggata tccctgtgga tgg                              33

SEQ ID NO: 27              moltype = DNA   length = 29
FEATURE                    Location/Qualifiers
source                     1..29
                           mol_type = other DNA
                           organism = synthetic construct
SEQUENCE: 27
tatcccgatt aaatatcggc cggccacgc                                   29

SEQ ID NO: 28              moltype = DNA   length = 30
```

```
FEATURE               Location/Qualifiers
source                1..30
                      mol_type = other DNA
                      organism = synthetic construct
SEQUENCE: 28
tatccatatg gctgctgccc atggtatatc                                        30

SEQ ID NO: 29         moltype = DNA   length = 34
FEATURE               Location/Qualifiers
source                1..34
                      mol_type = other DNA
                      organism = synthetic construct
SEQUENCE: 29
catcaaaaaa taacaccatc atcaccacag ccag                                   34

SEQ ID NO: 30         moltype = DNA   length = 40
FEATURE               Location/Qualifiers
source                1..40
                      mol_type = other DNA
                      organism = synthetic construct
SEQUENCE: 30
gaactctcat ccaattgaga tctgccatat gtatatctcc                             40

SEQ ID NO: 31         moltype = DNA   length = 55
FEATURE               Location/Qualifiers
source                1..55
                      mol_type = other DNA
                      organism = synthetic construct
SEQUENCE: 31
ggagatatac catgggcagc agccatatgg ataaaatcaa acagggtagc gctag            55

SEQ ID NO: 32         moltype = DNA   length = 39
FEATURE               Location/Qualifiers
source                1..39
                      mol_type = other DNA
                      organism = synthetic construct
SEQUENCE: 32
ggtgatgatg gtgttattta cgccacaggg tcaccatac                              39

SEQ ID NO: 33         moltype = DNA   length = 34
FEATURE               Location/Qualifiers
source                1..34
                      mol_type = other DNA
                      organism = synthetic construct
SEQUENCE: 33
tctcaattgg atgagagttc tggttaccgg tggt                                   34

SEQ ID NO: 34         moltype = DNA   length = 33
FEATURE               Location/Qualifiers
source                1..33
                      mol_type = other DNA
                      organism = synthetic construct
SEQUENCE: 34
gccgatattt aatcgggata tccctgtgga tgg                                    33

SEQ ID NO: 35         moltype = DNA   length = 29
FEATURE               Location/Qualifiers
source                1..29
                      mol_type = other DNA
                      organism = synthetic construct
SEQUENCE: 35
tatcccgatt aaatatcggc cggccacgc                                         29

SEQ ID NO: 36         moltype = DNA   length = 49
FEATURE               Location/Qualifiers
source                1..49
                      mol_type = other DNA
                      organism = synthetic construct
SEQUENCE: 36
ttgattttat ccatatggct gctgcccatg gtatatctcc ttattaaag                   49

SEQ ID NO: 37         moltype = DNA   length = 48
FEATURE               Location/Qualifiers
source                1..48
                      mol_type = other DNA
                      organism = synthetic construct
SEQUENCE: 37
ggtgaccctg tggcgtaaat aacaccatca tcaccacagc caggatcc                    48
```

```
SEQ ID NO: 38          moltype = DNA  length = 40
FEATURE                Location/Qualifiers
source                 1..40
                       mol_type = other DNA
                       organism = synthetic construct
SEQUENCE: 38
gaactctcat ccaattgaga tctgccatat gtatatctcc                              40
```

CONSTRUCTION METHOD AND APPLICATION OF MICROORGANISM CAPABLE OF REALIZING HIGH PRODUCTION OF LACTO-N-TETROSE

REFERENCE TO SEQUENCE LISTING

The instant application contains a Sequence Listing in XML format as a file named "YGHY-2022-85-seq.xml", created on Mar. 3, 2023, of 45 kB in size, and which is hereby incorporated by reference in its entirety.

TECHNICAL FIELD

The present disclosure relates to a construction method and application of a microorganism capable of realizing high production of lacto-N-tetrose, belonging to the field of microbial genetic engineering.

BACKGROUND

Studies have confirmed that human milk oligosaccharides (HMOs) have unique physiological functions such as regulating the balance of the intestinal microbiota of infants and young children, promoting early brain development of newborns, and improving immunity. Lacto-N-tetrose (LNT), one of the main components of the HMOs, is one of the twenty important core structures of the HMOs. With the lacto-N-tetrose as a core unit, a variety of HMOs can be prepared through fucosylation and sialylation. Therefore, the efficient preparation of the LNT plays an important role in the large-scale synthesis of a variety of HMOs. However, at present, the production costs of the lacto-N-tetrose and lacto-N-neotetraose are relatively high, and the production methods thereof are limited to a certain extent. Especially, as for the production of the lacto-N-tetrose, there is currently little research on its function and product synthesis.

At present, the lacto-N-tetrose can be obtained through chemical synthesis and biosynthesis. Chemical synthesis usually requires the introduction of protective groups, with cumbersome steps and problems such as inadequate protection, incomplete subsequent removal, and other side reactions, and often requires the use of toxic and harmful reagents. In contrast, biosynthesis is more suitable for large-scale industrial production due to its high specificity between enzymes and substrates, cheap substrates, simplified synthesis steps, fewer by-products, and greatly improved yield. The key gene encoding β-1,3-galactosyl transferase required for the current enzymatic production of the lacto-N-tetrose is derived from *Chromobacterium violaceum* or *Escherichia coli* O55:7.

SUMMARY

The present disclosure provides a recombinant *E. coli*, which expresses β-1,3-galactosyl transferase with an amino acid sequence as shown in SEQ ID NO.9, over-expresses glucosamine synthetase, UDP-acetyl glucosamine pyrophosphorylase, glucosamine-6-phosphate synthetase and β-1,3-acetyl glucosamine transferase, and knocks out a gene encoding UDP-N-acetyl glucosamine-2-epimerase, a gene encoding glucosamine-6 phosphate deaminase, and a gene encoding β-galactosidase.

In one implementation, the nucleotide sequence of a gene encoding the β-1,3-galactosyl transferase is as shown in SEQ ID NO.5.

In one implementation, the sequence number of the UDP-N-acetyl glucosamine-2-epimerase WecB is SEQ ID NO.12, the sequence number of the glucosamine-6 phosphate deaminase NagB is SEQ ID NO.13, and the sequence number of the β-galactosidase LacZ is SEQ ID NO.14.

In one implementation, a gene encoding the glucosamine synthetase is glmM, a gene encoding the UDP-acetyl glucosamine pyrophosphorylase is glmU, a gene encoding the glucosamine-6-phosphate synthetase is glmS, and the nucleotide sequences of the glmM, the glmU and the glmS are as shown in SEQ ID NO.1 to 3, respectively.

In one implementation, a gene encoding the β-1,3-acetyl glucosamine transferase is lgtA, and the nucleotide sequence of the lgtA is as shown in SEQ ID NO. 4.

In one implementation, the recombinant *E. coli* contains an expression vector pCDFDuet-1, and the expression vector contains a gene encoding the β-1,3-galactosyl transferase.

In one implementation, the recombinant *E. coli* contains expression vectors pRSFDuet-1 and pETDuet-1; the expression vector pRSFDuet-1 contains the genes encoding the glucosamine synthase, the UDP-acetyl glucosamine pyrophosphorylase and the glucosamine-6-phosphate synthetase; the expression vector pETDuet-1 contains the gene encoding the β-1,3-acetyl glucosamine transferase; the nucleotide sequence of a ribosome binding site on the pRSFDuet-1 is as shown in SEQ ID NO.10; and the nucleotide sequence of a ribosome binding site of the pETDuet-1 is as shown in SEQ ID NO.11.

The present disclosure provides a method for producing lacto-N-tetrose, and the recombinant *E. coli* is used as a fermentation strain.

In one implementation, the recombinant *E. coli* is cultured for 12-14 h to obtain seed liquid, the seed liquid is added to a reaction system containing glycerin in an amount being 2-5% of the volume of the reaction system and is subjected to shake culture at 35-40° C. until $OD_{600}$ is 0.6-0.8, IPTG with a final concentration of 0.1-0.2 mM is added to the reaction system, and induction culture is carried out at 22-25° C. for no less than 90 h.

In one implementation, the recombinant *E. coli* is cultured for 12-14 h to obtain seed liquid, the seed liquid is added to a reaction system in an amount being 2-5% of the volume of the reaction system and is subjected to shake culture at 35-40° C. until $OD_{600}$ is 14±3, IPTG with a final concentration of 0.1-0.2 mM and lactose with a final concentration of 5-10 g/L are added to the reaction system, and induction culture is carried out at 22-25° C. for no less than 40 h.

In one implementation, in the reaction process, the concentration of the lactose is maintained to be not less than 6 g/L, and the concentration of the glycerin is maintained to be not less than 10 g/L.

In one implementation, when the concentration of the glycerin in the reaction system is lower than 6 g/L, glycerin with a final concentration of 6 g/L is added at once; and when the concentration of the lactose in the reaction system is lower than 5 g/L, lactose with a final concentration of 5 g/L is added at once.

The present disclosure provides application of β-1,3-galactosyl transferase with an amino acid sequence as shown in SEQ ID NO.9 in production of lacto-N-tetrose.

In one implementation, the β-1,3-galactosyl transferase is employed to produce the lacto-N-tetrose under the condition that lacto-N-triose II and UDP-galactose are used as substrates.

The present disclosure provides application of the recombinant *E. coli* in the fields of food, biology and chemical industry.

The present disclosure provides application of the recombinant *E. coli* in preparation of the lacto-N-tetrose and derivatives thereof.

The Beneficial Effects of the Present Disclosure

The present disclosure screens the high-efficiency novel β-1,3-galactosyl transferase and applies same to fermentatively produce the lacto-N-tetrose. On the basis of the host for the efficient production of the lacto-N-triose II constructed by the team in the early stage, a novel gene Pf-β-1,3-GalT is over-expressed, the supply of a precursor UDP-galactose is enhanced, and the gene galE encoding UDP-glucose 4 epimerase is introduced, thus realizing the efficient production of the lacto-N-tetrose. In a shake flask experiment, the lacto-N-tetrose production capacity of the *E. coli* is 3.04 g/L. The lacto-N-tetrose yield in a 3 L fermentation tank reaches 25.49 g/L. Therefore, the microorganism has an industrial application prospect.

DETAILED DESCRIPTION

Figure 1:
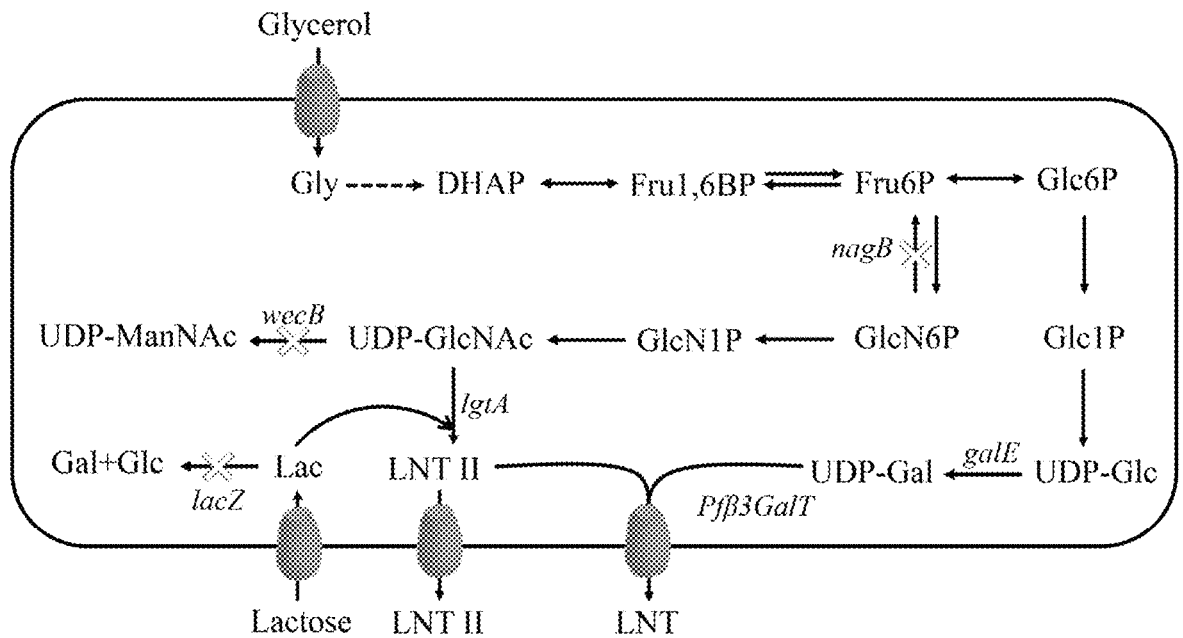
FIG. 1 is a diagram showing a metabolic pathway of lacto-N-tetrose.

1. The plasmids, endonucleases, PCR enzymes, column DNA extraction kits, DNA gel recovery kits, and the like used in the following examples are commercial products, and the specific operations thereof are carried out in accordance with the kit instructions.
2. Colony PCR, nucleic acid agarose gel electrophoresis, protein SDS-PAGE gel electrophoresis, heat shock transformation, electrotransformation, preparation of competent cells, extraction and preservation of bacterial genomes, and other conventional operation methods are carried out based on Molecular Cloning: A Laboratory Manual (Fourth Edition).
3. The sequencing of plasmids and DNA products was entrusted to Shanghai Sangon Biotech Company for completion.
4. Preparation of competent *E. coli*: TAKARA kit.
5. Medium and detection method for lacto-N-tetrose fermentation:
(1) LB liquid medium: 10 g/L of peptone, 5 g/L of a yeast extract, and 10 g/L of sodium chloride.
(2) LB solid medium: 10 g/L of peptone, 5 g/L of yeast extract powder, 10 g/L of sodium chloride, and 15 g/L of agar powder.
(3) Fermentation medium: 20 g/L of glucose, 13.5 g/L of potassium dihydrogenphosphate, 4.0 g/L of diammonium hydrogenphosphate, 1.7 g/L of citric acid, 1.4 g/L of magnesium sulfate heptahydrate, and 10 ml/L of trace metal elements; and the trace metal elements include: 10 g/L of ferrous sulfate, 2.25 g/L of zinc sulfate heptahydrate, 1.0 g/L of anhydrous copper sulfate, 0.35 g/L of manganese sulfate monohydrate, 0.23 g/L of sodium borate decahydrate, 0.11 g/L of ammonium molybdate, and 2.0 g/L of calcium chloride dihydrate.
(4) HPLC detection conditions: high-performance ion exchange chromatography; chromatographic column: CarboPac PA10 (4 mm×250 mm); detector: pulsed amperometric detector; mobile phase: A, ultrapure water; B, 1 M of sodium acetate; C, 250 mM of sodium hydroxide; flow rate: 1.0 mL/min; and injection volume: 20 μL.

Example 1: Construction of Recombinant Vector

The specific steps for constructing the recombinant expression vector were as follows (see Table 1 for primer sequences involved):
(1) Obtaining of gene fragments of genes glmM, glmU-glmS, and lgtA (the nucleotide sequences of the glmM, the glmU, the glmS, and the lgtA are as shown in SEQ ID NO.1 to 4, respectively) and the construction of plasmids pRSF-(29)glmM-(29)glmU-glmS and pET-(T7)lgtA, contained in Patent Publication No. CN111979168A.
(2) Obtaining of wbgO and galE gene fragments and construction of plasmid pCD-wbgO-galE A gene wbgO was synthesized by Suzhou GENEWIZ through codon optimization, and the nucleotide sequence of a wbgO gene fragment was as shown in SEQ ID NO.7. Under the conditions that the synthesized gene was used as a template, and WbgO-F/R was used as a primer, PCR amplification was performed to amplify the wbgO gene fragment, and DNA fragments were collected by means of gel extraction. Under the conditions that the genome of *E. coli* K-12 was used as a template, and WbgO-GalE-F/R was used as a primer, PCR amplification was performed to amplify a galE gene fragment (the nucleotide sequence of a gene galE was as shown in SEQ ID NO.6), and DNA fragments were collected by means of gel extraction. Two pairs of primers, i.e., WbgO-GalE-$V_1$-F/R and WbgO-GalE-$V_2$-F/R, were respectively used to amplify two vector fragments of pCDFDuet-1, and DNA fragments were collected by means of gel extraction. The four fragments obtained above were ligated by means of a Gibson kit (NEB Reagent Company, USA) to obtain a plasmid pCD-wbgO-galE.
(3) Obtaining of Cvβ3GalT and galE gene fragments and construction of plasmid pCD-cv-galE A gene Cvβ3GalT was synthesized by Suzhou GENEWIZ through codon optimization (the nucleotide sequence was as shown in SEQ ID NO.8). Under the conditions that the synthesized gene was used as a template, and Cv-F/R was used as a primer, PCR amplification was performed to amplify a Cvβ3GalT gene fragment, and DNA fragments were collected by means of gel extraction. Under the conditions that the genome of *E. coli* K-12 was used as a template, and Cv-GalE-F/R was used as a primer, PCR amplification was performed to amplify a galE gene fragment, and DNA fragments were collected by means of gel extraction. Two pairs of primers, i.e., Cv-GalE-$V_1$-F/R and Cv-GalE-$V_2$-F/R, were respectively used to amplify two vector fragments under the condition of using pCDFDuet-1 as a template, and DNA fragments were collected by means of gel extraction. The four fragments obtained above were ligated by means of a Gibson kit (NEB Reagent Company, USA) to obtain a plasmid pCD-cv-galE.

vector fragments under the condition of using pCDFDuet-1 as a template, and DNA fragments were collected by means of gel extraction. The four fragments obtained above were ligated by means of a Gibson kit (NEB Reagent Company, USA) to obtain a plasmid pCD-pf-galE.

TABLE 1

Primers for plasmid construction

| Primer name | Primer sequence (5'-3') | |
|---|---|---|
| WbgO-F | AGCAGCCATATGATCATCGATGAAGCGGAAAGC | SEQ ID NO. 15 |
| WbgO-R | GTGTTATTTGATGTATTTGCAGTAGATGAAGCTCGC | SEQ ID NO. 16 |
| WbgO-GalE-F | TCTCAATTGGATGAGAGTTCTGGTTACCGGTGGT | SEQ ID NO. 17 |
| WbgO-GalE-R | GCCGATATTTAATCGGGATATCCCTGTGGATGG | SEQ ID NO. 18 |
| WbgO-GalE-$V_1$-F | TATCCCGATTAAATATCGGCCGGCCACGC | SEQ ID NO. 19 |
| WbgO-GalE-$V_1$-R | ATGATCATATGGCTGCTGCCCATGGTATATC | SEQ ID NO. 20 |
| WbgO-GalE-$V_2$-F | CAAATACATCAAATAACACCATCATCACCACAGCCAG | SEQ ID NO. 21 |
| WbgO-GalE-$V_2$-R | GAACTCTCATCCAATTGAGATCTGCCATATGTATATCTCC | SEQ ID NO. 22 |
| Cv-F | AGCAGCCATATGGATACCATCATGATCAAACGTCCG | SEQ ID NO. 23 |
| Cv-R | ATGGTGTTATTTTTTGATGAAACGAACGTACAGGAACG | SEQ ID NO. 24 |
| Cv-GalE-F | TCTCAATTGGATGAGAGTTCTGGTTACCGGTGGT | SEQ ID NO. 25 |
| Cv-GalE-R | GCCGATATTTAATCGGGATATCCCTGTGGATGG | SEQ ID NO. 26 |
| Cv-GalE-$V_1$-F | TATCCCGATTAAATATCGGCCGGCCACGC | SEQ ID NO. 27 |
| Cv-GalE-$V_1$-R | TATCCATATGGCTGCTGCCCATGGTATATC | SEQ ID NO. 28 |
| Cv-GalE-$V_2$-F | CATCAAAAAATAACACCATCATCACCACAGCCAG | SEQ ID NO. 29 |
| Cv-GalE-$V_2$-R | GAACTCTCATCCAATTGAGATCTGCCATATGTATATCTCC | SEQ ID NO. 30 |
| Pf-F | GGAGATATACCATGGGCAGCAGCCATATGGATAAAATCAAACAGGGTAGCGCTAG | SEQ ID NO. 31 |
| Pf-R | GGTGATGATGGTGTTATTTACGCCACAGGGTCACCATAC | SEQ ID NO. 32 |
| Pf-GalE-F | TCTCAATTGGATGAGAGTTCTGGTTACCGGTGGT | SEQ ID NO. 33 |
| Pf-GalE-R | GCCGATATTTAATCGGGATATCCCTGTGGATGG | SEQ ID NO. 34 |
| Pf-GalE-$V_1$-F | TATCCCGATTAAATATCGGCCGGCCACGC | SEQ ID NO. 35 |
| Pf-GalE-$V_1$-R | TTGATTTTATCCATATGGCTGCTGCCCATGGTATATCTCCTTATTAAAG | SEQ ID NO. 36 |
| Pf-GalE-$V_2$-F | GGTGACCCTGTGGCGTAAATAACACCATCATCACCACAGCCAGGATCC | SEQ ID NO. 37 |
| Pf-GalE-$V_2$-F | GAACTCTCATCCAATTGAGATCTGCCATATGTATATCTCC | SEQ ID NO. 38 |

(4) Obtaining of Pf-β-1,3-GalT and galE gene fragments and construction of plasmid pCD-pf-galE A gene Pf-β-1,3-GalT was synthesized by Suzhou GENEWIZ through codon optimization (the nucleotide sequence was as shown in SEQ ID NO.5). Under the conditions that the synthesized gene was used as a template, and Pf-F/R was used as a primer, PCR amplification was performed to amplify a Pf-β-1,3-GalT gene fragment, and DNA fragments were collected by means of gel extraction. Under the conditions that the genome of *E. coli* K-12 was used as a template, and Pf-GalE-F/R was used as a primer, PCR amplification was performed to amplify a galE gene fragment, and DNA fragments were collected by means of gel extraction. Two pairs of primers, i.e., Pf-GalE-$V_1$-F/R and Pf-GalE-$V_2$-F/R, were respectively used to amplify two Example 2: Construction of Recombinant Strains A gene wecB encoding UDP-N-acetyl glucosamine-2-epimerase WecB (NCBI sequence number: YP_026253.1, which is set forth in SEQ ID NO.12), a gene nagB encoding glucosamine-6 phosphate deaminase NagB (NCBI sequence number: NP_415204.1, which is set forth in SEQ ID NO.13), and a gene lacZ encoding β-galactosidase LacZ (NCBI sequence number: NCBI NP_414878.1, which is set forth in SEQ ID NO.14) in *E. coli* BL21 were knocked out, and the recombinant plasmids pRSF-(29)glmM-(29)glmU-glmS and pET-(T7)lgTA constructed in Example 1 were transferred to the *E. coli*. For the gene knockout and recombinant plasmid transfer methods, please refer to Patent Publication No. CN111979168A. The recombinant *E. coli* E10-WNL for producing lacto-N-triose II was constructed.

(1) The recombinant plasmid pCD-wbgO-galE constructed in Example 1 was transferred into *E. coli* E10-WNL to construct a recombinant strain EL01.

(2) The recombinant plasmid pCD-pf-galE constructed in Example 1 was transferred into *E. coli* E10-WNL to construct a recombinant strain EL02.

(3) The recombinant plasmid pCD-cv-galE constructed in Example 1 was transferred into *E. coli* E10-WNL to construct a recombinant strain EL03.

Example 3: Fermentation of Recombinant Strains to Produce Lacto-N-Tetrose

Fermentation process of lacto-N-tetrose: the 3 recombinant strains constructed in Example 2 were respectively inoculated into an LB liquid medium and cultured overnight for 12 h under the conditions of 37° C. and 200 rpm to obtain seed liquid; the seed liquid was inoculated into a 25 ml fermentation medium (containing 20 g/L glycerin) in an inoculation dosage of 2 mL/100 mL under the conditions of 37° C. and 200 rpm, and cultured until $OD_{600}$ is 0.6; and IPTG with a final concentration of 0.2 mM was added, lactose with a final concentration of 5 g/L was added at the same time, and induction culture was continued for 96 h under the conditions of 25° C. and 200 rpm. 1 mL of fermentation broth was taken and centrifuged at 10,000 rpm for 10 min, and supernatant was extracted for HPLC determination.

Figure 2A:
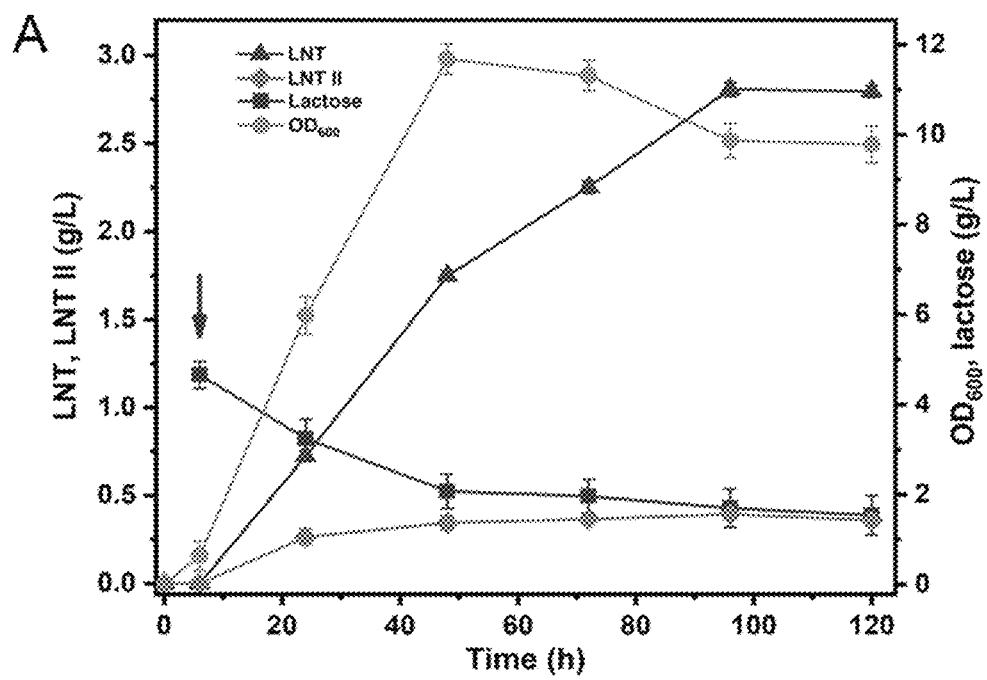
FIG. 2A is a diagram showing the yield of lacto-N-tetrose biosynthesized by β-1,3-galactosyl transferase (WbgO) derived from *E. coli* O55:H7.

The fermentation result of the recombinant strain expressing the reported β-1,3-galactosyl transferase derived from *E. coli* O55:H7 is as shown in FIG. 2A. After 96 h of fermentation, the yield of lacto-N-tetrose produced by the strain reaches 2.81 g/L, accompanied by the yield of residual lacto-N-triose II of 0.39 g/L.

Figure 2B:
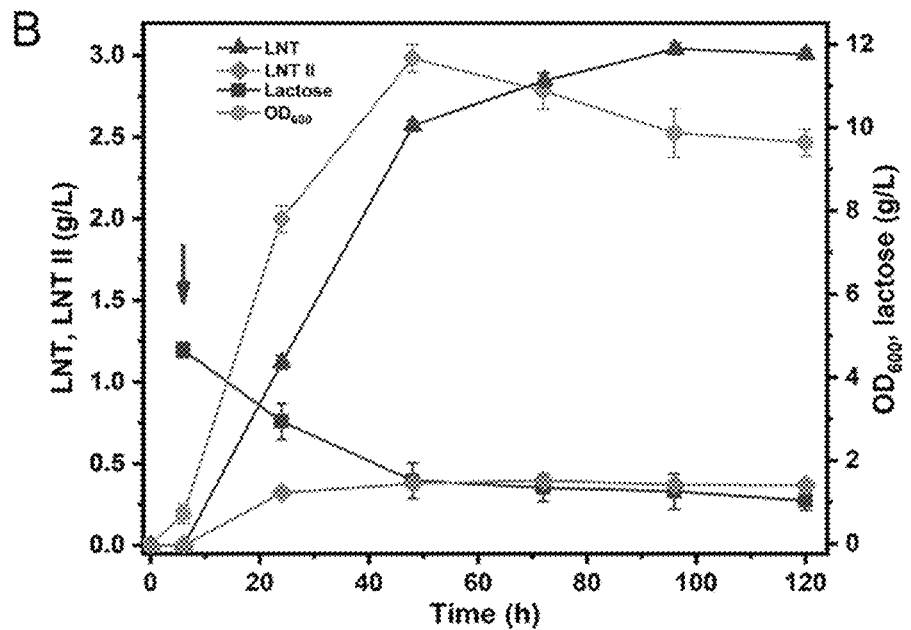
FIG. 2B is a diagram showing the yield of lacto-N-tetrose biosynthesized by β-1,3-galactosyl transferase (Pf-β-1,3-GalT) derived from *P. ferrooxidans*.
Figure 2C:
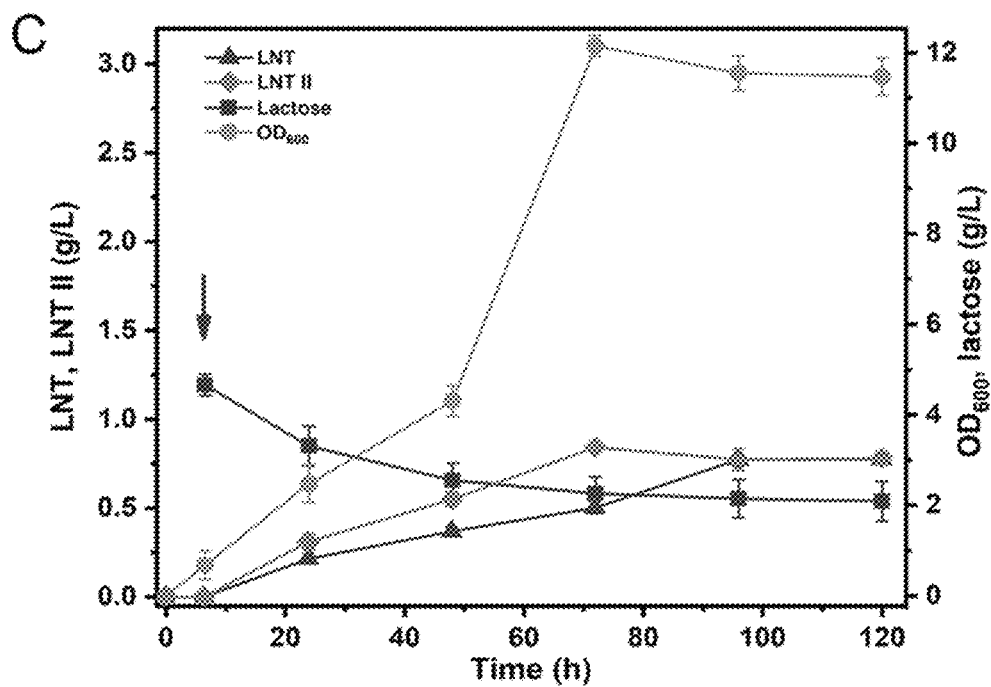
FIG. 2C is a diagram showing the yield of lacto-N-tetrose biosynthesized by β-1,3-galactosyl transferase (Cvβ3GalT) derived from *C. violaceum*.

The fermentation result of the recombinant strain expressing the reported β-1,3-galactosyl transferase derived from *C. violaceum* is as shown in FIG. 2C. After 96 h of fermentation, the yield of lacto-N-tetrose produced by the strain reaches 0.77 g/L, accompanied by the yield of residual lacto-N-triose II of 0.77 g/L.

The fermentation result of the recombinant strain expressing the newly screened β-1,3-galactosyl transferase derived from *P. ferrooxidans* is as shown in FIG. 2B. After 96 h of fermentation, the yield of lacto-N-tetrose produced by the strain reaches 3.04 g/L, accompanied by the yield of residual lacto-N-triose II of 0.37 g/L.

Figure 3A:
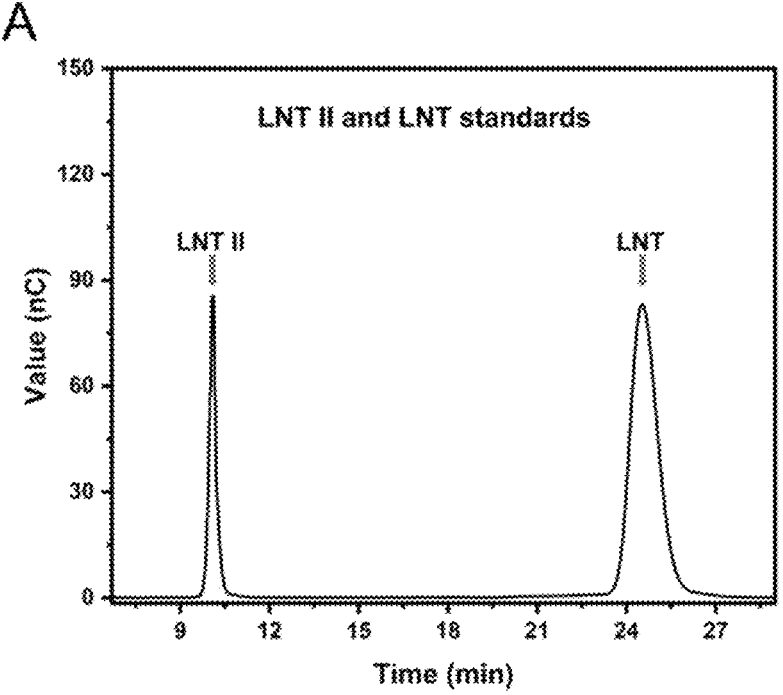
FIG. 3A to FIG. 3C are liquid phase diagrams and mass spectra of a lacto-N-tetrose product standard sample and a lacto-N-tetrose product sample.
Figure 3B:
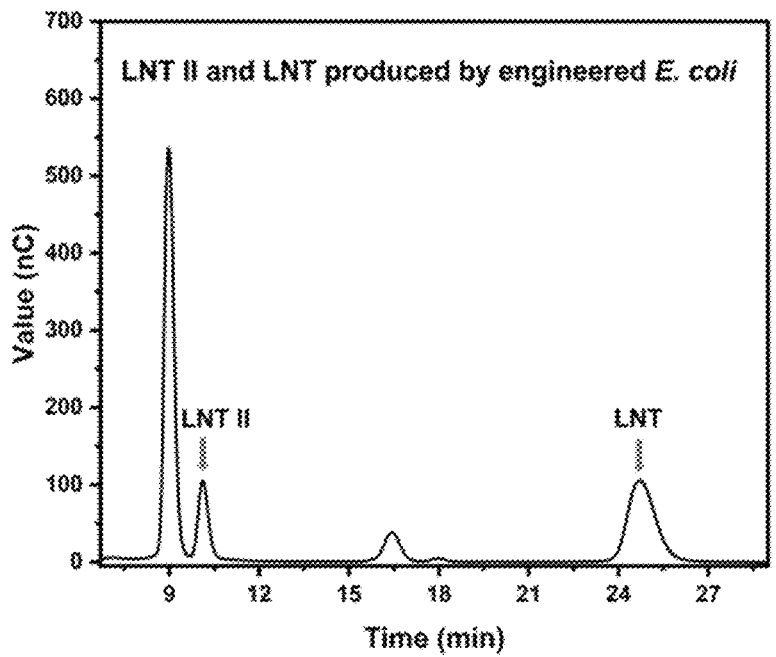
Figure 3C:
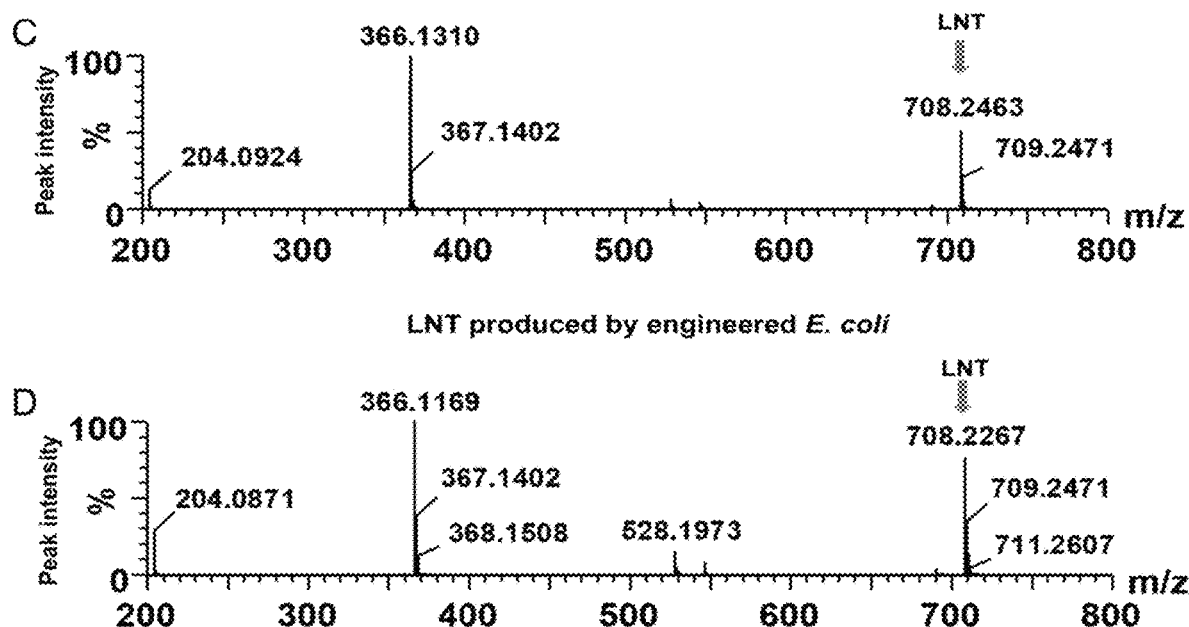

Liquid phase diagrams and mass spectra of a lacto-N-tetrose standard sample and a product sample are as shown in FIG. 3A to FIG. 3C.

Figure 4:
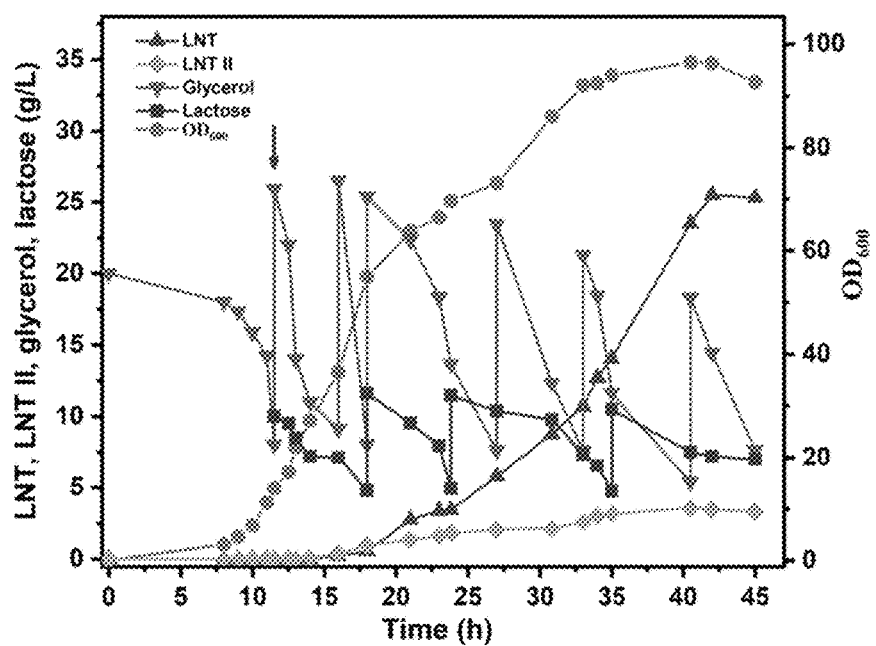
FIG. 4 is a resulting diagram showing the fermentation yield of lacto-N-tetrose in a 3 L fermentation tank.

Example 4: Engineered Strain Fermentation Tank with Efficient Production to Produce Lacto-N-Tetrose In order to further verify the effectiveness of the synthesis method of lacto-N-tetrose and increase the lacto-N-tetrose yield, the seed liquid of recombinant *E. coli* EL02 was inoculated into a fermentation medium with a working volume of 1 L in an inoculation dosage of 10%, where the fermentation temperature of a fermentation tank was 37° C., the stirring speed was 800 r/min, the ventilation volume was 1 vvm, and the pH was 7.0 (automatically controlled by supplementing ammonia water). Fermentation was performed for 11.5 h ($OD_{600}$ was approximately 14), lactose with a final concentration of 10 g/L and IPTG with a final concentration of 0.2 mM were added, and culturing was carried out at 25° C. During the culturing, glycerin and lactose were manually supplemented to maintain the growth of the strain and the synthesis of the lacto-N-tetrose: when the concentration of the lactose in the reaction system was below 6 g/L, 30 mL of lactose mother liquor (with a concentration of 200 g/L) was supplemented, and when the concentration of the glycerin was below 10 g/L, 30 mL of glycerin mother liquor (with a concentration of 600 g/L) was supplemented. After the entire culturing process reached 42 h, the $OD_{600}$ of the strain reached 96.3, and the yield of the lacto-N-tetrose was the maximum, reaching up to 25.49 g/L (see FIG. 4).

TABLE 2

Dynamic changes in synthetic amount of strains and lacto-N-tetrose during fermentation

| | Time (h) | | | | | | | | |
|---|---|---|---|---|---|---|---|---|---|
| | 10 | 11.5 | 14 | 18 | 23 | 27 | 34 | 40.5 | 42 |
| $OD_{600}$ | 6.8 | 14 | 27.3 | 55 | 66.4 | 73 | 92.46 | 96.54 | 96.3 |
| Lacto-N-tetrose (g/L) | 0 | 0 | 0 | 0.54 | 2.76 | 5.78 | 12.7 | 23.5 | 25.49 |
| Lacto-N-triose II (g/L) | 0 | 0 | 0.07 | 0.94 | 1.34 | 2.05 | 2.99 | 3.58 | 3.44 |
| Glycerin (g/L) | 15.9 | 8.1 | 11 | 8.1 | 22.36 | 7.63 | 18.46 | 5.4 | 14.45 |
| Lactose (g/L) | 0 | 10 | 7.2 | 4.81 | 9.54 | 10.4 | 6.53 | 7.5 | 7.2 |

Although the present disclosure has been disclosed as above in exemplary examples, it is not intended to limit the present disclosure. Anyone familiar with this technology can make various changes and modifications without departing from the spirit and scope of the present disclosure. Therefore, the protection scope of the present disclosure shall be as defined in the Claims.

What is claimed is:

1. A recombinant *Escherichia coli*, wherein β-1,3-galactosyl transferase with the amino acid sequence as set forth in SEQ ID NO:9 is expressed, wherein glucosamine synthetase, UDP-acetyl glucosamine pyrophosphorylase, glucosamine-6-phosphate synthetase and β-1,3-acetyl glucosamine transferase are over-expressed, and wherein a gene encoding UDP-N-acetyl glucosamine-2-epimerase, a gene encoding glucosamine-6 phosphate deaminase, and a gene encoding β-galactosidase are disrupted.

2. The recombinant *E. coli* according to claim 1, wherein the recombinant *E. coli* contains an expression vector pCDFDuet-1, and the expression vector contains a gene encoding the β-1,3-galactosyl transferase.

3. The recombinant *E. coli* according to claim 1, wherein the sequence of the NCBI YP_026253.1 UDP-N-acetyl glucosamine-2-epimerase WecB is set forth in SEQ ID NO:12, the sequence of the NCBI NP_415204.1 glucosamine-6 phosphate deaminase NagB is set forth in SEQ ID NO: 13, and the sequence of the NCBI NP_414878.1 β-galactosidase LacZ is set forth in SEQ ID NO:14.

4. The recombinant *E. coli* according to claim 1, wherein a gene encoding the glucosamine synthetase is glmM, a gene encoding the UDP-acetyl glucosamine pyrophosphorylase is glmU, a gene encoding the glucosamine-6-phosphate synthetase is glmS, and the nucleotide sequences of the glmM, the glmU and the glmS are as set forth in SEQ ID NO: 1 to 3, respectively.

5. The recombinant *E. coli* according to claim 1, wherein a gene encoding the β-1,3-acetyl glucosamine transferase is IgtA, and the nucleotide sequence of the IgtA is as set forth in SEQ ID NO: 4.

6. The recombinant *E. coli* according to claim 1, containing expression vectors pRSFDuet-1 and pETDuet-1, wherein the expression vector pRSFDuet-1 contains the genes encoding the glucosamine synthase, the UDP-acetyl glucosamine pyrophosphorylase and the glucosamine-6-phosphate synthetase; the expression vector pETDuet-1 contains the gene encoding the β-1,3-acetyl glucosamine transferase; the nucleotide sequence of a ribosome binding site on the pRSFDuet-1 is as set forth in SEQ ID NO.10; and the nucleotide sequence of a ribosome binding site of the pETDuet-1 is as set forth in SEQ ID NO: 11.

7. A method for producing lacto-N-tetrose, wherein the recombinant *E. coli* according to claim 1 is used as a fermentation strain.

8. The method according to claim 7, wherein the recombinant *E. coli* is cultured for 12 hours to 14 hours to obtain seed liquid, the seed liquid is added to a reaction system containing glycerin in an amount being 2% to 5% of the volume of the reaction system and is subjected to shake culture at 35° C. to 40° C. until $OD_{600}$ is 0.6 to 0.8, isopropyl β-d-1-thiogalactopyranoside (IPTG) with a final concentration of 0.1 mM to 0.2 mM is added to the reaction system, and induction culture is carried out at 22° C. to 25° C. for no less than 90 hours.

9. The method according to claim 8, wherein the recombinant *E. coli* is cultured for 12 hours to 14 hours to obtain seed liquid, the seed liquid is added to a reaction system in an amount being 2% to 5% of the volume of the reaction system and is subjected to shake culture at 35° C. to 40° C. until $OD_{600}$ is 14±3, IPTG with a final concentration of 0.1 mM to 0.2 mM and lactose with a final concentration of 5 g/L to 10 g/L are added to the reaction system, and induction culture is carried out at 22° C. to 25° C. for no less than 40 hours.

10. The method according to claim 9, wherein in the reaction process, the concentration of the lactose is maintained to be not less than 6 g/L, and the concentration of the glycerin is maintained to be not less than 10 g/L.

11. The method according to claim 10, wherein when the concentration of the glycerin in the reaction system is lower than 6 g/L, glycerin with a final concentration of 6 g/L is added at once.

12. The method according to claim 11, wherein when the concentration of the lactose in the reaction system is lower than 5 g/L, lactose with a final concentration of 5 g/L is added at once.

* * * * *